(12) United States Patent
Farley

(10) Patent No.: US 10,639,198 B2
(45) Date of Patent: May 5, 2020

(54) MULTI-FIBER MULTI-SPOT LASER PROBE WITH ARTICULATING BEAM SEPARATION

(71) Applicant: Novartis AG, Basel (CH)

(72) Inventor: Mark Farley, Laguna Hills, CA (US)

(73) Assignee: Alcon Inc., Fribourg (CH)

( * ) Notice: Subject to any disclaimer, the term of this patent is extended or adjusted under 35 U.S.C. 154(b) by 162 days.

(21) Appl. No.: 15/988,586

(22) Filed: May 24, 2018

(65) Prior Publication Data

US 2018/0344528 A1 Dec. 6, 2018

Related U.S. Application Data

(60) Provisional application No. 62/512,483, filed on May 30, 2017.

(51) Int. Cl.
| | | |
|---|---|---|
| *A61F 9/008* | (2006.01) | |
| *A61F 9/009* | (2006.01) | |
| *A61B 18/22* | (2006.01) | |
| *A61B 18/20* | (2006.01) | |

(52) U.S. Cl.
CPC .......... *A61F 9/00823* (2013.01); *A61F 9/009* (2013.01); *A61B 2018/208* (2013.01); *A61B 2018/2216* (2013.01); *A61B 2018/2238* (2013.01); *A61F 2009/0087* (2013.01); *A61F 2009/00863* (2013.01)

(58) Field of Classification Search
CPC ................. A61F 9/008; A61F 9/009
See application file for complete search history.

(56) References Cited

U.S. PATENT DOCUMENTS

| | | | |
|---|---|---|---|
| 5,351,678 A | * | 10/1994 | Clayton ............ A61B 1/00179 600/114 |
| 5,402,508 A | | 3/1995 | O'Rourke et al. |
| 5,746,738 A | | 5/1998 | Cleary |
| 6,096,028 A | | 8/2000 | Bahmanyar et al. |
| 7,566,173 B2 | | 7/2009 | Auld et al. |
| 8,561,280 B2 | | 10/2013 | Diao et al. |
| 8,571,364 B2 | | 10/2013 | Smith et al. |
| 8,764,261 B2 | | 7/2014 | Smith |
| 8,939,964 B2 | | 1/2015 | Smith |

(Continued)

FOREIGN PATENT DOCUMENTS

| | | |
|---|---|---|
| EP | 1667588 A2 | 6/2006 |
| WO | 9908612 A1 | 2/1999 |

(Continued)

*Primary Examiner* — Carl H Layno
*Assistant Examiner* — Jon Eric C Morales

(57) ABSTRACT

An example probe multi-spot, multi-fiber, laser probe includes a plurality of optical fibers extending from a proximal end of the laser probe to at least near a distal end of the laser probe, and a cannula having a distal end and surrounding the plurality of optical fibers along at least a portion of the laser probe at or near the distal end of the laser probe. A distal pass-through element is positioned within the cannula and at or near the distal end of the cannula and has a groove and/or channel corresponding to each fiber and through which a respective optical fiber passes, and is formed so as to induce a radial rotation of each of the plurality of optical fibers, relative to a central longitudinal axis of the cannula, as the respective optical fiber passes through the distal pass-through element.

14 Claims, 6 Drawing Sheets

(56) References Cited

U.S. PATENT DOCUMENTS

| | | |
|---|---|---|
| 8,951,244 B2 | 2/2015 | Smith |
| 2001/0012429 A1 | 8/2001 | Wach et al. |
| 2002/0045811 A1 | 4/2002 | Kittrell et al. |
| 2003/0125719 A1 | 7/2003 | Furnish |
| 2007/0265602 A1 | 11/2007 | Mordaunt et al. |
| 2008/0051770 A1 | 2/2008 | Scheller et al. |
| 2008/0249517 A1* | 10/2008 | Svanberg ............ A61N 5/0601 606/15 |
| 2009/0015923 A1 | 1/2009 | Auld et al. |
| 2009/0270850 A1 | 10/2009 | Zhou et al. |
| 2009/0287197 A1 | 11/2009 | Hanley et al. |
| 2013/0097843 A1 | 4/2013 | Diao et al. |
| 2013/0150839 A1 | 6/2013 | Smith et al. |
| 2014/0180264 A1 | 6/2014 | Diao et al. |
| 2014/0194862 A1 | 7/2014 | Smith et al. |
| 2014/0200566 A1 | 7/2014 | Smith |
| 2014/0250668 A1 | 9/2014 | Smith |
| 2015/0241614 A1 | 8/2015 | Ide et al. |
| 2016/0062041 A1 | 3/2016 | Lee et al. |
| 2016/0120699 A1* | 5/2016 | Farley ................ A61F 9/00736 606/4 |
| 2016/0220310 A1 | 8/2016 | Taylor et al. |

FOREIGN PATENT DOCUMENTS

| | | |
|---|---|---|
| WO | 2004/016155 A2 | 2/2004 |
| WO | 2008024848 A2 | 2/2008 |
| WO | 2008024848 A3 | 6/2008 |
| WO | 2006/121407 A1 | 11/2008 |
| WO | 2011/037651 A1 | 3/2011 |

\* cited by examiner

MULTI-FIBER MULTI-SPOT LASER PROBE WITH ARTICULATING BEAM SEPARATION

TECHNICAL FIELD

This application relates to a laser probe for use in ophthalmic procedures and more particularly to a multi-spot laser probe for use in photocoagulation.

BACKGROUND

Laser photocoagulation therapy addresses ocular conditions such as retinal detachments and tears as well as proliferative retinopathy resulting from diseases such as diabetes. The abnormally high blood sugar in a diabetic stimulates the retinal vessels to release growth factors that in turn encourage an undesirable proliferation of blood vessels and capillaries over the retinal surface. These proliferated blood vessels are very delicate and will readily bleed into the vitreous. The body responds to the damaged vessels by producing scar tissue, which may then cause the retina to detach so as to eventually cause blindness.

In laser photocoagulation, a laser probe is used to cauterize the blood vessels at various laser burn spots across the retina. Because the laser will also damage the rods and cones that are present in the retina to allow vision, eyesight, as well as the blood vessels, is affected. Since vision is most acute at the central macula of the retina, the surgeon arranges the resulting laser burn spots in the peripheral areas of the retina. In this fashion, some peripheral vision is sacrificed to preserve central vision. During the procedure, the surgeon drives the probe with a non-burning aiming beam such that the retinal area to be photocoagulated is illuminated. Due to the availability of low-power red laser diodes, the aiming beam is generally a low-power red laser light. Once the surgeon has positioned the laser probe so as to illuminate a desired retinal spot, the surgeon activates the laser through a foot pedal or other means to then photocoagulate the illuminated area. Having burned a retinal spot, the surgeon repositions the probe to illuminate a new spot with the aiming light, activates the laser, repositions the probe, and so on until a suitable array of burned laser spots are distributed across the retina.

The number of required laser photocoagulations for any one treatment of the retina is large. For example, 1,000 to 1,500 spots are commonly burned. It may thus be readily appreciated that if the laser probe was a multi-spot probe enabling the burning of multiple spots at a time, the photocoagulation procedure would be faster (assuming the laser source power is sufficient). Accordingly, multi-spot laser probes have been developed and can be classified into two categories. A first category, denoted herein as a "multi-spot/multi-fiber" laser probe, produces its multiple laser beams through a corresponding array of optical fibers. A second category uses only a single optical fiber and is thus denoted herein as a "multi-spot/single-optical fiber" laser probe. Regardless of whether a laser probe is a single-optical fiber or multi-fiber probe, it should be compatible with the adapter used to connect the probes to the laser source. In that regard, it is conventional for a laser source to have a standardized interconnect such as a subminiature version A (SMA) interconnect. For example, the laser source may have a female SMA connector that receives a male SMA connector coupled to whatever instrument the laser source is driving. For a conventional single-spot/single-optical fiber laser probe, its male SMA connector will incorporate a single optical fiber. The laser source provides a focused beam known as the laser beam waist to the male SMA connector. This is quite advantageous for the single optical fiber probe since its optical fiber has its end face illuminated by the waist to enable efficient coupling to the laser source. But if a multi-spot/multi-fiber laser probe uses a corresponding plurality of optical fibers to drive its multiple spots, it cannot simply have its multiple optical fibers receive the focused beam from the source in this convenient single-optical fiber fashion because the laser waist is too narrow to couple into multiple optical fibers. Instead, the laser source would have to have its conventional interconnect changed or adapted so that the multiple optical fibers from the probe are not simply presented with the laser waist. But such changes are expensive and cumbersome.

Thus, a multi-spot/multi optical fiber probe has been developed such that the laser source drives a single optical fiber interconnect connected to a single optical fiber cable that in turn drives a single-optical fiber/multiple-optical fiber optical coupling within the laser probe handpiece. The resulting optics within the handpiece increase costs because it is desirable that the laser probe be disposable to limit contamination from patient to patient. For example, the optics include a diffractive beam splitter to split the beam from the single optical fiber into multiple beams for distribution to the multiple optical fibers. To collimate the laser beam from the single optical fiber onto the beam splitter and then condense the resulting multiple beams onto the multiple optical fibers requires plano-convex lenses. But it is very difficult to move such lenses to the laser source interconnect such that the remainder of the probe can be less expensive because of the relatively small inner diameter of such interconnects.

Another issue arises in multi-spot/multi-fiber laser probes in that the telecentric laser beams transmitted from the distal ends of the multiple optical fibers should be directed into different angular directions so as to properly distribute the resulting laser beam spots on the retina. To provide such distribution, a multi-spot/multi-fiber laser probe has been developed with the distal ends of the optical fibers bent into the desired angular directions. But such bending is cumbersome and increases costs as well.

To avoid the issues associated with the use of multiple optical fibers, the light beam from a single-optical fiber laser probe can be directed onto a diffractive beam splitter that splits the beam into multiple diffracted beams for transmission to the retina. However, the diffractive beam splitter must then focus the resulting diffracted beams, which requires the grating prescription to be spatially varying across the element. Not only does such a complication increase costs, the resulting spatially-varying diffractive beam splitter will reduce the overall performance. Such a design also makes varying the distance between the distal optical fiber end the diffractive element difficult.

Accordingly, there is a need in the art for improved multi-spot laser probes.

SUMMARY

Several embodiments of the multi-fiber laser probes disclosed herein provide for multi-spot beam delivery; in some cases providing for the selective delivery of single-spot or multi-spot beam patterns. An example probe multi-spot, multi-fiber, laser probe according to some of the embodiments detailed herein includes a plurality of optical fibers extending from a proximal end of the laser probe to at least near a distal end of the laser probe, where the proximal end of the laser probe is configured to be coupled to a laser source via an adapter interface. The laser probe further includes a cannula having a distal end and surrounding the plurality of optical fibers along at least a portion of the laser probe at or near the distal end of the laser probe, and a distal pass-through element positioned within the cannula and at or near the distal end of the cannula. The distal pass-through element has a groove and/or channel corresponding to each of the optical fibers and through which a respective optical fiber passes, the grooves and/or channels extending through the distal pass-through element, and is formed so as to induce a radial rotation of each of the plurality of optical fibers, relative to a central longitudinal axis of the cannula, as the respective optical fiber passes through the distal pass-through element, and so that each of the plurality of optical fibers is positioned to emit light in a distinct and divergent angular direction, with respect to a direction substantially parallel to the central longitudinal axis of the cannula.

Other embodiments of the multi-spot, multi-fiber, laser probes described herein also include a plurality of optical fibers extending from a proximal end of the laser probe to at least near a distal end of the laser probe, and also include a cannula having a distal end and surrounding the plurality of optical fibers along at least a portion of the laser probe at or near the distal end of the laser probe. These further embodiments further include a distal pass-through element affixed to and positioned within the cannula and at or near the distal end of the cannula, with the distal pass-through element having a groove and/or channel corresponding to each of the optical fibers and through which a respective optical fiber passes, the grooves and/or channels extending through the distal pass-through element in a longitudinal direction, with respect to the cannula. In these embodiments, the cannula is configured to be rotatable around its central axis, relative to the plurality of fibers, along with the affixed distal pass-through element, from a first rotational position in which all of the plurality of fibers are substantially parallel to one another and substantially parallel to a central longitudinal axis of the cannula while passing through the distal pass-through element, to any of a range of other rotational positions in which the grooves and/or channels of the distal pass-through element induce a radial rotation of each of the plurality of optical fibers, relative to a central longitudinal axis of the cannula. In these other rotational positions, the distal end of each of the plurality of optical fibers is positioned to emit light in a distinct and divergent angular direction, with respect to a direction substantially parallel to the central longitudinal axis of the cannula.

In some of any of the embodiments summarized above, the distal pass-through element may comprise an additional channel extending through the distal pass-through element at or near the central longitudinal axis of the cannula, and the laser probe may further include an additional optical fiber extending from the proximal end of the laser probe to at least near the distal end of the laser probe, through the additional channel, so that the additional optical fiber is positioned to emit light in the direction substantially parallel to the central longitudinal axis of the cannula.

DETAILED DESCRIPTION

Described in detail herein are improved multi-spot/multi-fiber laser probes that are compatible with conventional laser source interconnects.

Figure 1:
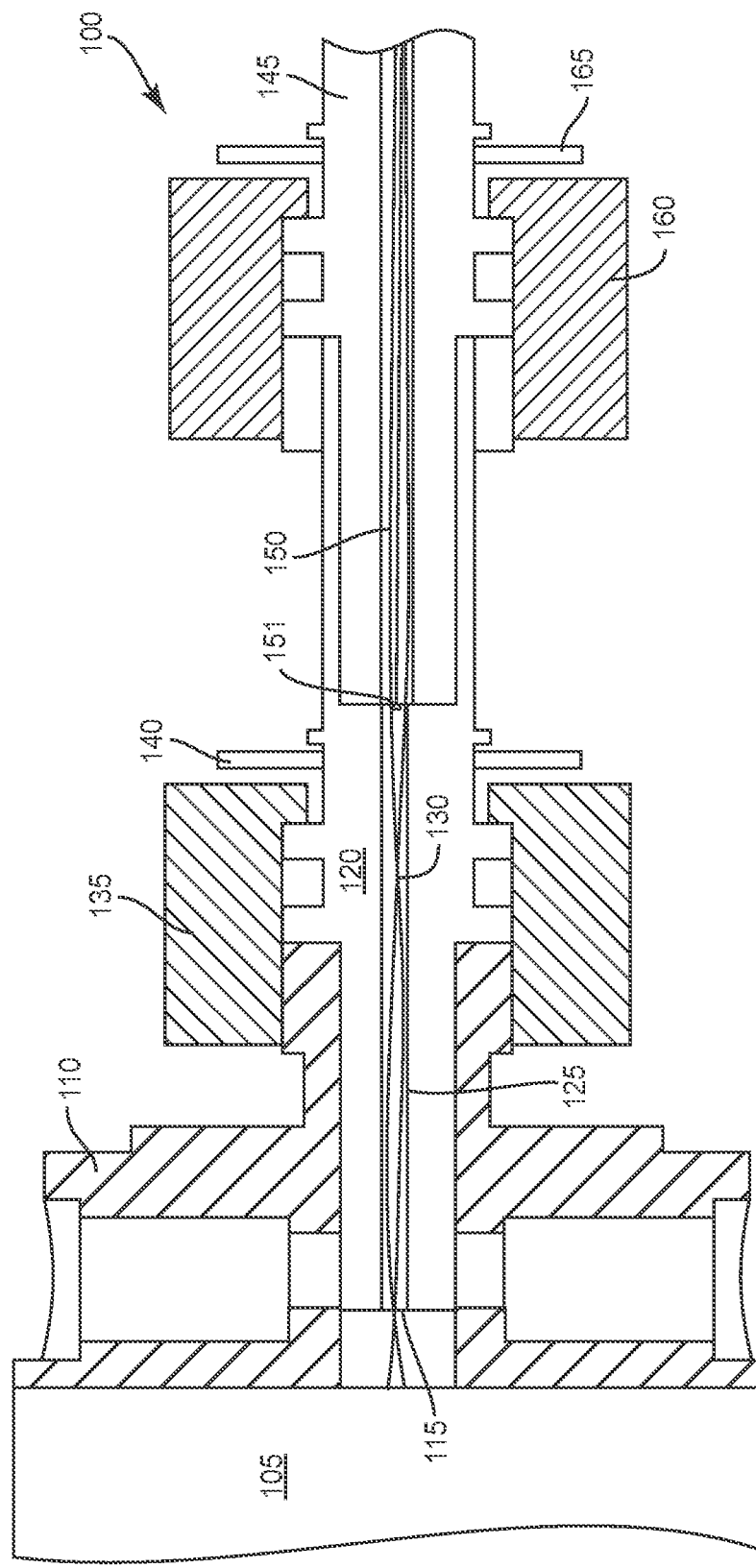
FIG. 1 is a longitudinal cross-sectional view of a laser source coupled to an adapter element containing a gradient-index (GRIN) lens for coupling to a proximal end of a multi-spot/multi-fiber laser probe.

Turning now to the drawings, certain details of a multi-spot/multi-fiber laser probe 100 are shown in FIG. 1. Not shown in FIG. 1 are details of the proximal end of laser probe 100; details of several realizations of the proximal end are provided below. The portions of the multi-spot/multi-fiber laser probe 100 shown in FIG. 1 are also illustrated in U.S. Pat. No. 8,951,244; thus, it will be appreciated that the details shown in FIG. 1 represent an example of the prior art.

Returning to FIG. 1, it can be seen that a laser source 105 drives probe 100 through a suitable interconnect. A common standardized interconnect for laser source 105 is a subminiature version A (SMA) adapter. Thus, laser source 105 includes a female SMA adapter 110. However, it will be appreciated that laser probe 100 is readily adapted to mate with any conventional standardized optical interconnect so long as the laser source's interconnect presents a focused beam spot such as laser waist 115 to a proximal end of a male connector from the laser probe. Thus, the following discussion will assume that laser probe 100 couples to source 105 through a customized SMA adapter 120 without loss of generality.

To receive laser waist 115, the bore of SMA adapter 120 includes a gradient index (GRIN) lens 125. GRIN lens 125 may be a simple, single-element cylindrical GRIN rod lens that is readily inserted into such a bore. GRIN lens 125 is designed to relay the focused beam to a second focused spot 130 and then to a collimated beam wave front at its distal end. As known in the SMA arts, SMA adapter 120 secures to SMA adapter 110 through a threaded cylinder 135 and retaining ring 140. SMA adapter 120 has both a male end for insertion into SMA adapter 110 but also a female end that receives a conventional optical interconnect such a male SMA 905 optical fiber connector 145. Connected 145 secures to adapter 120 through a threaded cylinder or ring 160 and retaining ring 165. Connector 145 includes in its bore an array of optical fibers 150. A proximal end 151 of array 150 is separated from the distal end of GRIN lens 125 by a suitable air gap such as a 220 μm air gap. Connector 145 connects to a flexible cable encasing optical fibers 150 that leads to a handpiece and cannula, as known in the laser probe arts.

Figure 2:
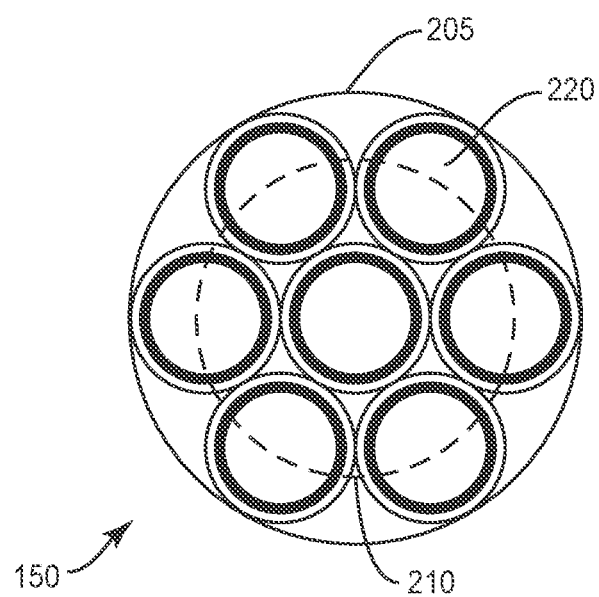
FIG. 2 shows a radial cross-sectional view of a multi-fiber array within the proximal end of the probe of FIG. 1.

An example embodiment of optical fiber array 150 is shown in cross-section in FIG. 2. The laser beam boundary at the proximal end 151 of FIG. 1 is shown for both a green laser beam boundary 205 from source 105 as well as a red aiming beam boundary 210. Array 150 includes a central optical fiber circumferentially surrounded by six outer optical fibers. In one embodiment, each optical fiber 220 has a numerical aperture (NA) of 0.22 achieved through a 75 µm glass core encased in a 90 µm cladding, surrounded by a 101 µm jacket. To minimize the amount of uncoupled laser energy into array 150, GRIN lens 125 is configured such that laser beam boundary 205 just encompasses the six outer optical fibers. The clocking of array 150 relative to the laser beam is not an issue as the laser beam and array 150 are at least generally axisymmetric. Array 150 extends to a distal end of the laser probe; details of several embodiments of the distal end of the laser probe are discussed in more detail below.

The advantageous properties of such a proximal interconnection in that no complicated, multi-lens relay system is required. Instead, GRIN lens 125 is readily inserted into the bore of adapter 120 that enables a standardized adapter such as male SMA adapter 145 to attach a disposable laser probe receiving optical fiber array 150. Without GRIN lens 125 and its adapter 120, standardized adapter 110 on laser source 105 would have to be changed, which is plainly undesirable since other attachments for source 105 would have to change in concert. Alternatively, the source's adapter could be left standardized but then a multi-lens relay system would be required. However, SMA adapter 120 and GRIN lens 125 eliminate such complications. Although SMA adapter 120 is thus quite advantageous, one can appreciate that roughly 50% of the laser energy is delivered to the interstices between the optical fibers in array 150 as seen in FIG. 2. This laser energy is thus unavailable for use in photocoagulation, thereby increasing the necessary laser source power and/or the amount of time necessary to produce the laser burn spots.

Figure 3:
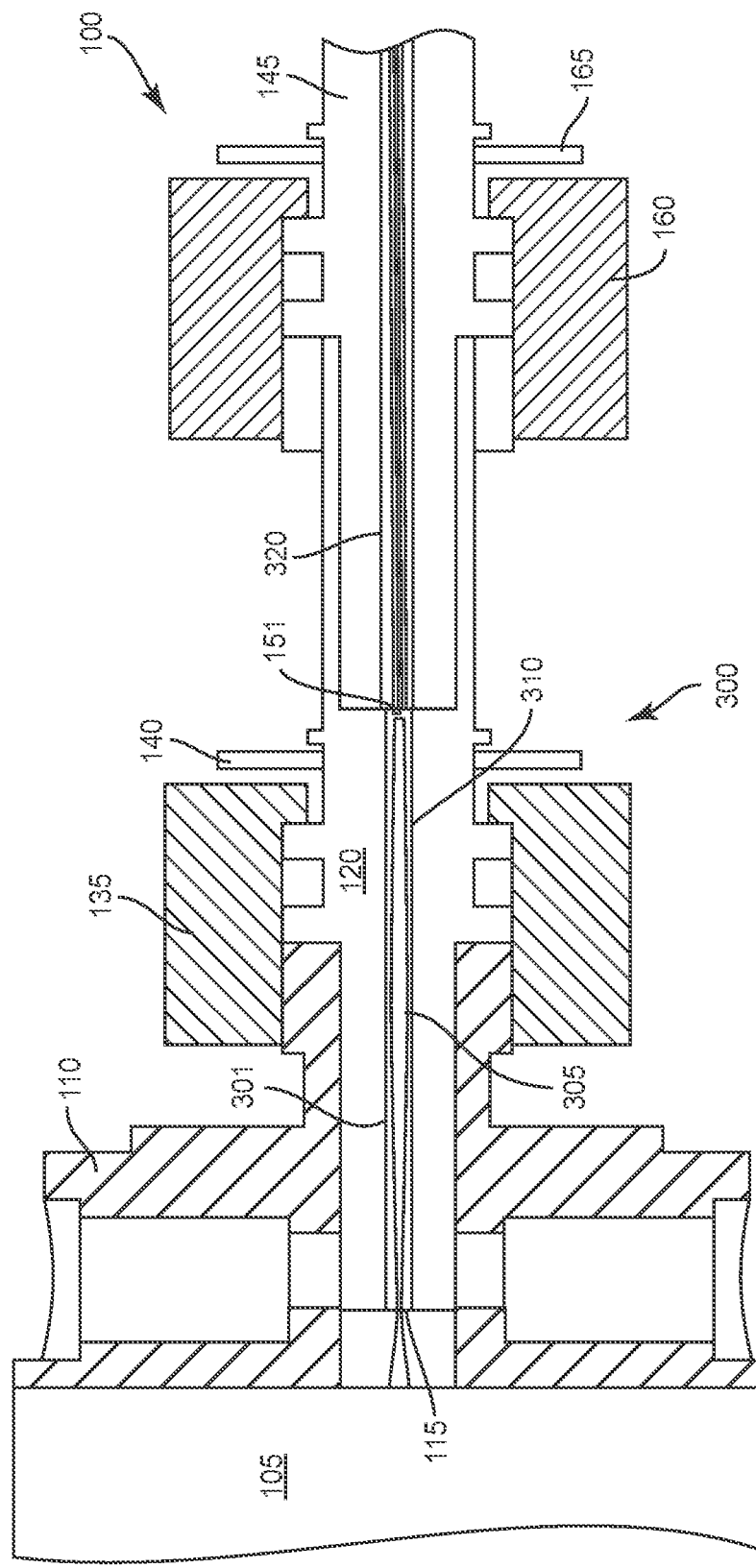
FIG. 3 is a longitudinal cross-sectional view of a laser source coupled to an adapter element including a diffractive beam splitter for coupling to a proximal end of a multi-spot/multi-fiber laser probe.
Figure 4:
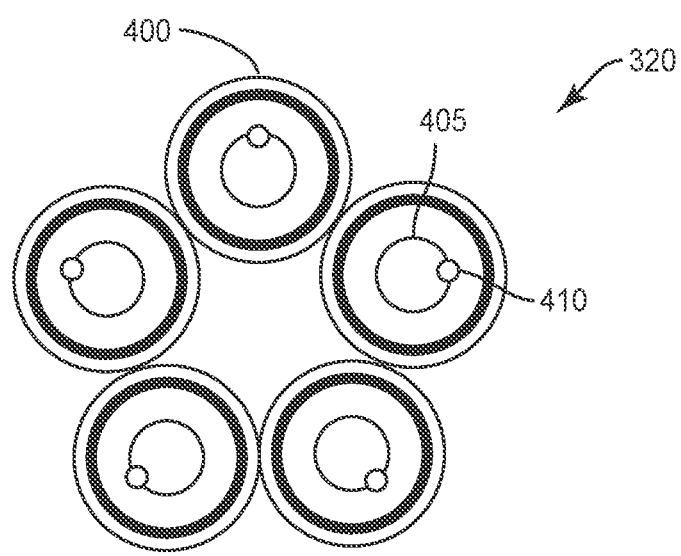
FIG. 4 is a radial cross-sectional view of a multi-fiber array within the proximal end of the probe of FIG. 3.

Turning now to FIG. 3, a diffractive embodiment that does not illuminate optical fiber array interstices is illustrated. As discussed with regard to FIG. 1, customized SMA adapter 120 permits a user to conveniently attach a disposable probe to adapter 120 to drive laser energy onto a optical fiber array. In the embodiment shown in FIG. 1, however, adapter 120 includes in its bore a diffractive beam splitter 305 arranged between a first GRIN lens 301 and a second GRIN lens 310. GRIN lens 301 is configured to collimate the laser beam diverging from laser waist 115 into a collimated wave front presented to diffractive beam splitter 305. GRIN lens 310 is configured to focus the resulting diffracted multiple laser beams from splitter 305 onto a proximal face 151 of a optical fiber array 320 contained within the bore of male SMA adapter 145. Optical fiber array 320 includes a plurality of optical fibers arranged according to the diffractive properties of diffractive beam splitter 305. For example, if diffractive beam splitter produces a symmetric pentagonal distribution of five diffracted beams, optical fiber array 320 is arranged in a corresponding pentagonal distribution. FIG. 4 shows such an arrangement for optical fiber bundle 320 at its proximal face 151.

In one embodiment, each optical fiber 400 has a 75 µm glass core clad in a 90 µm cladding, which in turn is surrounded by a 101 µm jacket, to achieve an NA of 0.22. The resulting projection of the diffracted green laser beams from splitter 305 is indicated by a boundary 405. Because diffraction is wavelength dependent, the projection of the aiming beam will have a different alignment with optical fiber array 320. Thus, splitter 305 and optical fiber array 320 are arranged such that boundary 405 is axially aligned with each optical fiber 400, whereas a boundary 410 of a red aiming beam is radially displaced with regard to a center or longitudinal axis of each optical fiber.

In one embodiment, the off-axis displacement provided by splitter 305 to each green diffracted beam is 1.45 degrees. GRIN lens 310 focuses the resulting collimated and diffracted beams onto the entrance face of each optical fiber 400 in array 320. By such an appropriate clocking of array 320 relative to the diffracted beams, efficient coupling of the respective diffracted beam and the aiming beam into each optical fiber 400 is achieved. In that regard, other types of adapters such as a ferrule connector (FC) or a standard connector (SC) commonly used in the telecommunications industry may be used instead of SMA adapter 120 to assist in optimal clocking. As discussed with regard to FIG. 1, assembly of the optical components into SMA adapter 120 is advantageously convenient in that GRIN lenses 301 and 310 as well as intervening diffractive beam splitter 305 may have optical adhesive applied and then slid into the bore of adapter 120 and abutted end-to-end with each other. In contrast, an alignment of refractive lenses would be cumbersome and difficult in comparison.

Figure 5:
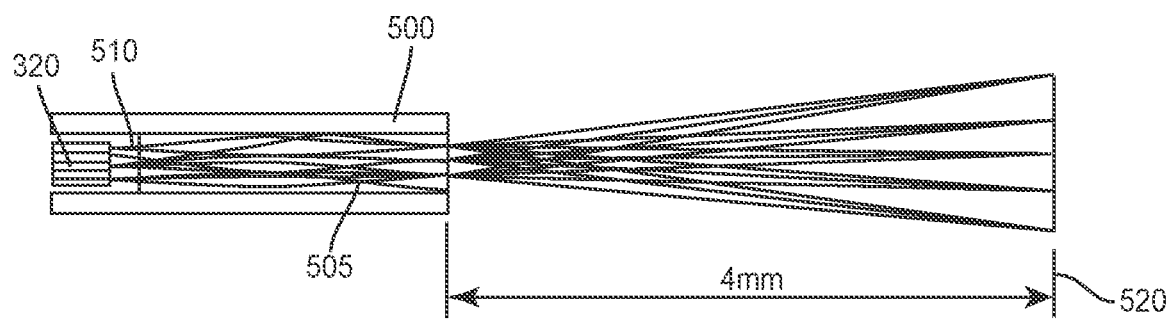
FIG. 5 illustrates a GRIN lens for angularly separating the projected multiple beams emitted from the multi-fiber array of FIG. 4.

With the laser beam from the source split and telecentrically propagated through the optical fiber array as discussed above with regard to either FIG. 1 or FIG. 3, there remains the issue of angularly projecting focused laser spots from the laser probe. U.S. Pat. No. 8,951,244 disclosed a GRIN lens solution, an example of which is shown in FIG. 5. It will be appreciated that while the example embodiment shown in FIG. 5 is particularly adapted for compatibility with the optical fiber array 320 of FIG. 3, it will be appreciated that an analogous embodiment can be readily constructed for optical fiber array 150 of FIG. 1.

As seen in FIG. 5, a laser probe cannula 500, e.g., a stainless-steel cannula, receives a GRIN lens 505 at its distal end. A distal end of optical fiber array 320 is displaced within the cannula so as to project diverging beams 510 at a proximal end face of GRIN lens 505. GRIN lens 505 then focuses the beams on the retinal surface 520. The distribution of the resulting focused beams on the retina depends on the distribution of the optical fibers at the distal end of array 320.

In that regard, whereas the distribution at the proximal end of array 320 (FIG. 3) should be axially symmetric, one can arrange the optical fibers in any suitable distribution at the distal end. For example, as seen in FIG. 5, array 320 is linearly arranged at the distal end. The resulting laser spots are thus an enlarged version of the image (in this embodiment, a linear array) presented to GRIN lens 505. In one embodiment, GRIN lens 505 focuses the angularly-distributed beams at a distance of 4 mm from the distal end of cannula 500. Advantageously, GRIN lens 505 obviates any need for: bending the optical fibers into the desired angular distribution (and the associated problems of such bending), beveling the distal end faces of the optical fibers, or adding optical elements to the distal end faces. The optical fibers can even be touching one another in array 320 and GRIN lens 505 will still be effective.

In the following, several alternatives to the configuration shown in FIG. 5 for the distal end of a multi-fiber laser probe are described in detail. These embodiments have in common that the GRIN lens 505 is removed from the laser beam path at the probe's distal end. Indeed, several of the embodiments described in detail below have no optical elements distal to the optical fibers. Test data have shown certain GRIN lens materials to be susceptible to thermal failure due to increased absorption caused by photodarkening and/or moisture ingress through the anti-reflective coating. The increased absorption leading to this failure mode is associated with certain GRIN lens chemistries, and may be alleviated by embodiments that eliminate the use of optics distal to the laser transmission optical fibers, or that use distal optics made from non-GRIN materials, such as pure fused silica. It will be appreciated, then, that the several embodiments detailed herein may improve thermal reliability, while providing optical performance similar to the device shown in FIG. 5.

The embodiments detailed below further provide a variety of actuation means to induce angular beam separation, via helical curvature of the optical fibers. Various embodiments provide advantages such as small-gauge compatibility and/or switchable quasi-single-spot and multi-spot beam delivery.

The several embodiments detailed below are presented with respect to 4-optical fiber or 5-optical fiber embodiments of the invention, which are shown in axial and transverse cross section views. It will be understood, however, that the number of optical fibers is not limited to 4 or 5—fewer or more optical fibers may be used, in various embodiments. Further, the embodiments are not presented in any particular order. The embodiments disclosed herein may be implemented in laser probes that are compatible with either of the adapters described above, i.e., in FIGS. 1 and 3, which provide means for splitting the beam and focusing the resulting multiple beams into the proximal ends of optical fibers, such each optical fiber carries its own beam. It will be understood, however, that the embodiments described below may be implemented in laser probes having different mating configurations at the proximal end, and/or in conjunction with different adapters or interfaces for coupling a laser source or sources to the multiple optical fibers of the multi-fiber laser probe.

Figure 6:
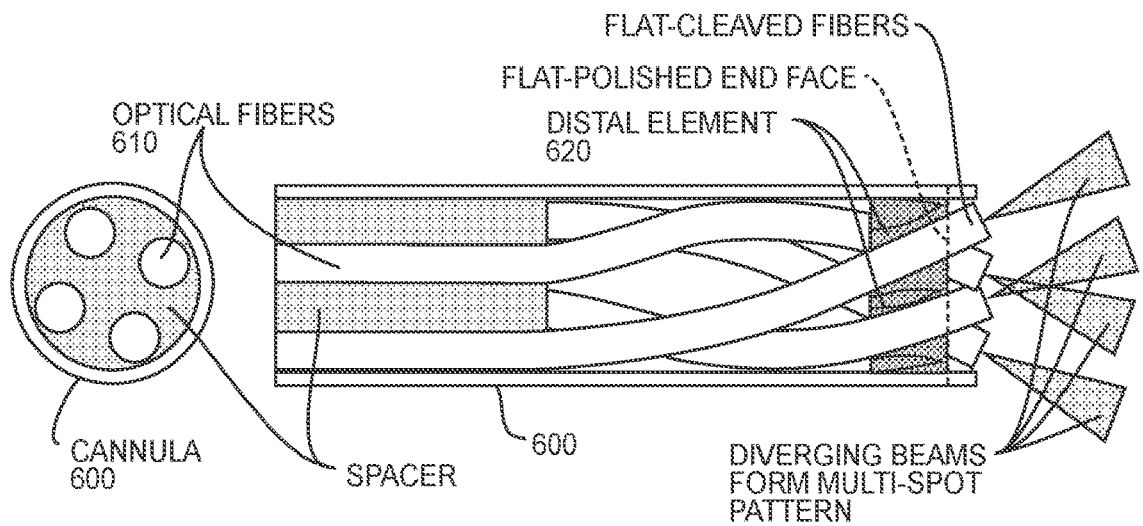
FIG. 6 illustrates an example embodiment of a distal end of a multi-fiber multi-spot laser probe.

A first example embodiment of the distal end of a multi-fiber multi-spot laser probe that omits a GRIN lens at the distal end is shown in FIG. 6. As seen in the figures, this example laser probe includes a distal pass-through element 620 positioned within the cannula 600, at or near the distal end of the cannula, and having passages, i.e., grooves and/or channels, through which the fibers 610 pass. These grooves and/or channels are rotated about the axis of the cannula 600, relative to the axes of their corresponding proximal fibers, so as to induce a radial rotation of each optical fiber 610, relative to the central longitudinal axis of the cannula, as the optical fiber 610 passes through the distal pass-through element 620. In this manner, the fibers can be induced to form a helix, with suitable rotation angle to achieve the desired angular separation of the fibers at their output, corresponding to a desired spot spacing. As can be seen in FIG. 6, each of the optical fibers 610 is thus positioned to emit light in a distinct and divergent angular direction, with respect to a direction substantially parallel to the central longitudinal axis of the cannula 620. The fibers 610 may optionally be flat cleaved or flat-polished, e.g., with an end-face angle of only a few degrees, which may simplify manufacturability and provide a sealed end with enhanced moisture resistance, cleanliness, and durability. The ends may be flat polished to an angle of less than about 5 degrees, for example.

The embodiment illustrated in FIG. 6, as is the case with the others disclosed herein, may incorporate tapered distal cross section profiles to modify the output beam characteristics. For example, the distal fibers may be tapered to a larger cross section near the distal end in order to reduce the beam divergence. Conversely, the fibers may be tapered to a smaller cross section to increase the beam divergence.

Figure 7:
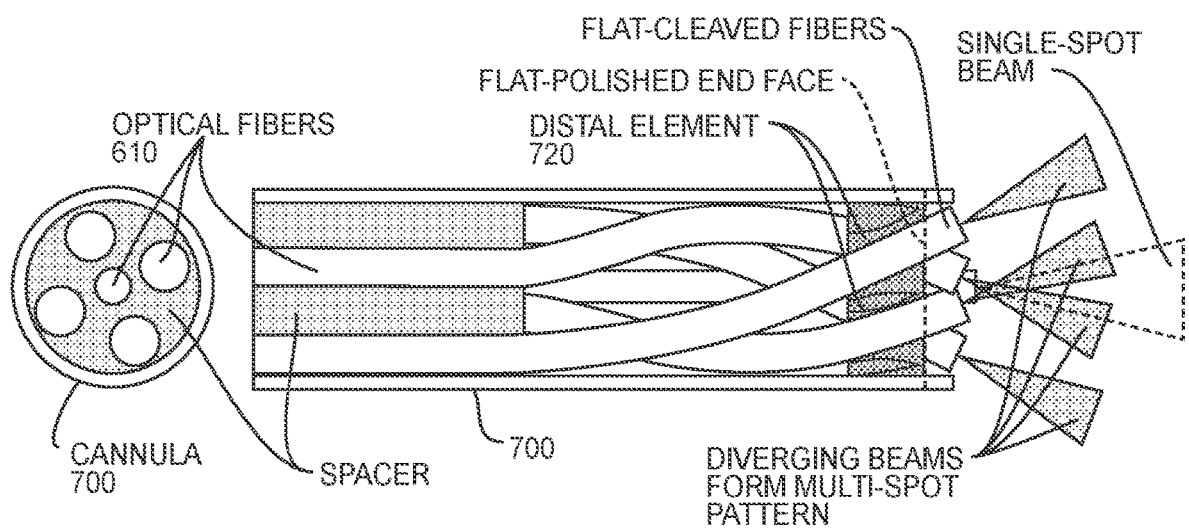
FIG. 7 illustrates another example embodiment of a distal end of a multi-fiber multi-spot laser probe.

FIG. 7 shows the distal end of another example laser probe. The configuration shown in FIG. 7 includes the same features and provides the same advantages as that shown in FIG. 6. In the embodiment shown in FIG. 7, however, the distal pass-through element 720 comprises an additional channel extending through the distal pass-through element 720 at or near the central longitudinal axis of the cannula 700. This allows for an additional optical fiber, extending from the proximal end of the laser probe to pass through the additional channel, so that the additional optical fiber is positioned to emit light in the direction substantially parallel to the central longitudinal axis of the cannula. Depending on how the illumination of the fibers is controlled, this allows for the selective application of a single spot-beam, from this central additional fiber, or the combination of a central spot beam with a surrounding multi-spot pattern. Note that while a single additional fiber is shown passing through the additional channel of distal pass-through element 720, in FIG. 7, other embodiments might include multiple fibers passing through this additional channel, or through several channels positioned near the center of the distal pass-through element 720.

The central fiber or fibers may be the same or similar type as the surrounding fibers, in some embodiments, or it may be different, in others. The central fiber may be routed to a separate source at the input end of the laser probe, in some embodiments, so as to deliver the same wavelength and beam characteristics as the other fibers, but in a single beam used simultaneously or alternately. This independent single-beam delivery capability can provide complementary functionality in complex surgeries, and may address a greater variety of uses, for example where multi-spot delivery is advantageous for procedures such as pan-retinal photocoagulation (PRP), but where single-spot delivery is advantageous for other procedures, such as the repair of retinal breaks and tears. In some embodiments, this additional fiber may also be of a different type, e.g., so as to provide for simultaneous or alternate delivery of different optical wavelengths and beam characteristics, e.g., for providing broad-spectrum, wide-angle illumination, or for receiving light for sensing purposes, such as in a reflective proximity sensor.

Figure 8A:
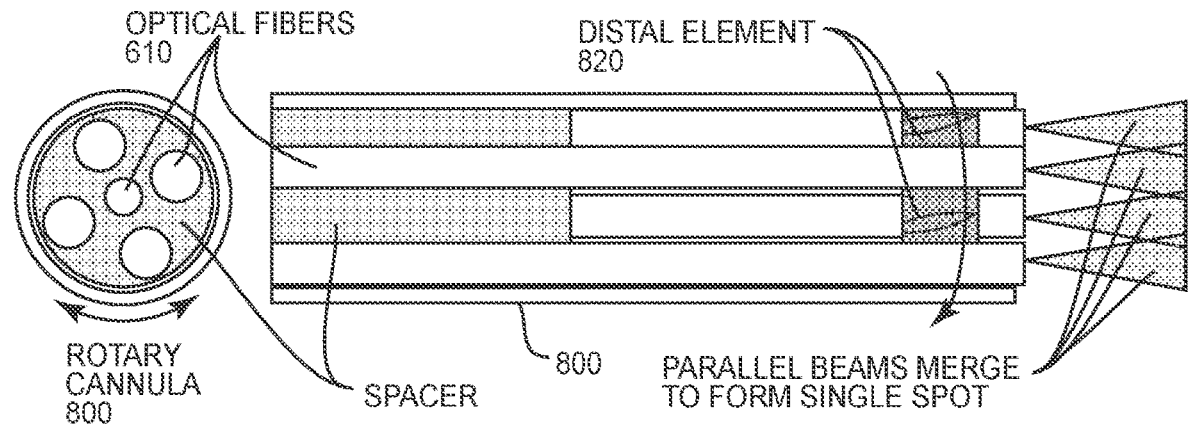
FIG. 8A and FIG. 8B illustrate the distal end of another multi-fiber multi-spot laser probe, which provides adjustable or selectable spot spacing.
Figure 8B:
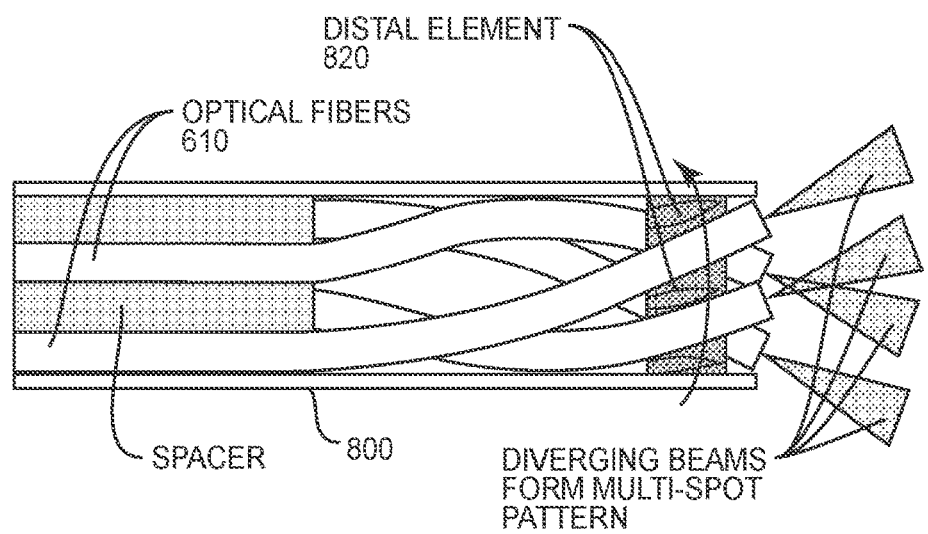

FIG. 8A and FIG. 8B illustrate the distal end of another example laser probe. This embodiment provides similar advantages to those provided by the embodiment shown in FIG. 6, and can be modified to provide an additional, central fiber like the embodiment shown in FIG. 7. However, the embodiment shown in FIGS. 8A and 8B provides adjustable or selectable spot spacing, which can deliver either a pattern of parallel beams that merge to form essentially a single spot (quasi-single-spot) or a diverging multi-spot beam pattern. This is accomplished by a distal pass-through element 820 that may be attached to the cannula 800, and having grooves and/or channels extending through the distal pass-through element and through which the optical fibers 610 pass. The distal pass-through element 820 can be rotated, along with the cannula 800, relative to the optical fibers 610. In this manner, the probe can be switched from multi-spot delivery to single-spot delivery by rotating the cannula and distal element relative to the fibers by a suitable angle to achieve a desired angular separation of the fibers at their output ends corresponding to the desired spot spacing. FIG. 8*a* illustrates the example embodiment in a first rotational position for the cannula 800 and distal pass-through element 820, in which all of the plurality of fibers are substantially parallel to one another and substantially parallel to a central longitudinal axis of the cannula 800 while passing through the distal pass-through element. FIG. 8B, on the other hand, shows one example of a range of other rotational positions for the cannula 800 and distal pass-through element 820, in which the grooves and/or channels of the distal pass-through element 820 induce a radial rotation of each of the optical fibers 610, relative to a central longitudinal axis of the cannula 800, so that the distal end of each of optical fibers 610 is positioned to emit light in a distinct and divergent angular direction, with respect to a direction substantially parallel to the central longitudinal axis of the cannula 800.

The embodiment shown in FIGS. 8A and 8B thus comprises fibers 610, with cleaved or flat-polished ends, that are rotatable as a group through a distal pass-through element 820, so as to achieve either of two states: quasi-single-spot beam delivery, or multi-spot beam delivery.

The several embodiments described herein and illustrated in FIGS. 6-8, and variants thereof, may solve several problem, while providing similar optical performance to previously available devices, such as the device described in U.S. Pat. No. 8,951,244. The thermal reliability of the device may be improved, by removing optical elements from the beam path distal to the optical fibers. The relative rotary positioning of fiber and probe elements preserves small-gauge compatibility, and may be implemented so as to provide the ability to use the probe in a single-spot or multi-spot delivery mode. Employing a helical or roughly helical configuration for the optical fibers provides a tangential component to the optical fiber positioning, thus achieving fiber angular separation within the smallest possible instrument diameter. Some embodiments may include an open central region useful to run an open lumen or an auxiliary fiber of either the same or different type as the surrounding fibers, e.g., for use as a single-spot laser delivery, illumination, sensing or other uses.

The embodiments described above illustrate, but do not limit, the invention. It should also be understood that numerous modifications and variations are possible in accordance with the principles of the present invention.

What is claimed is:

1. A multi-spot, multi-fiber, laser probe, comprising:
   a plurality of optical fibers extending from a proximal end of the laser probe to at least near a distal end of the laser probe, wherein the proximal end of the laser probe is configured to be coupled to a laser source via an adapter interface;
   a cannula having a distal end and surrounding the plurality of optical fibers along at least a portion of the laser probe at or near the distal end of the laser probe; and
   a distal pass-through element positioned within the cannula and at or near the distal end of the cannula, the distal pass-through element having a groove or channel corresponding to each of the optical fibers and through which a respective optical fiber passes, the grooves or channels extending through the distal pass-through element and being formed to induce a radial rotation of each of the plurality of optical fibers, relative to a central longitudinal axis of the cannula, as the respective optical fiber passes through the distal pass-through element, so that each of the plurality of optical fibers is positioned to emit light in a distinct and divergent angular direction, with respect to a direction substantially parallel to the central longitudinal axis of the cannula.

2. The multi-spot, multi-fiber, laser probe of claim 1, wherein the distal pass-through element comprises an additional channel extending through the distal pass-through element at or near the central longitudinal axis of the cannula, and wherein the laser probe further comprises an additional optical fiber extending from the proximal end of the laser probe to at least near the distal end of the laser probe, through the additional channel, so that the additional optical fiber is positioned to emit light in the direction substantially parallel to the central longitudinal axis of the cannula.

3. The multi-spot, multi-fiber, laser probe of claim 1, wherein the distal end of each of one or more of the plurality of optical fibers is flat cleaved.

4. The multi-spot, multi-fiber, laser probe of claim 1, wherein the distal end of each of one or more of the plurality of optical fibers is flat polished, to an end-angle of less than about 5 degrees.

5. The multi-spot, multi-fiber, laser probe of claim 1, wherein each of one or more of the plurality of fibers has a tapered cross-sectional profile along a portion of the respective fiber at or near the distal end of the respective fiber.

6. The multi-spot, multi-fiber, laser probe of claim 5, wherein the tapered cross-sectional profile for at least one of the one or more of the plurality of fibers tapers to a larger cross section near the distal end of the respective fiber, relative to a cross section further from the distal end of the respective fiber.

7. The multi-spot, multi-fiber, laser probe of claim 5, wherein the tapered cross-sectional profile for at least one of the one or more of the plurality of fibers tapers to a smaller cross section near the distal end of the respective fiber, relative to a cross section further from the distal end of the respective fiber.

8. A multi-spot, multi-fiber, laser probe, comprising:
   a plurality of optical fibers extending from a proximal end of the laser probe to at least near a distal end of the laser probe, wherein the proximal end of the laser probe is configured to be coupled to a laser source via an adapter interface;
   a cannula having a distal end and surrounding the plurality of optical fibers along at least a portion of the laser probe at or near the distal end of the laser probe; and
   a distal pass-through element affixed to and positioned within the cannula and at or near the distal end of the cannula, the distal pass-through element having a groove or channel corresponding to each of the optical fibers and through which a respective optical fiber passes, the grooves or channels extending through the distal pass-through element in a longitudinal direction, with respect to the cannula;
   wherein the cannula is configured to be rotatable around its central axis, relative to the plurality of fibers, along with the affixed distal pass-through element, from (i) a first rotational position in which all of the plurality of fibers are substantially parallel to one another and substantially parallel to a central longitudinal axis of the cannula while passing through the distal pass-through element, to (ii) any of a range of other rotational positions in which the grooves or channels of the distal pass-through element induce a radial rotation of each of the plurality of optical fibers, relative to a central longitudinal axis of the cannula, so that the distal end of each of the plurality of optical fibers is positioned to emit light in a distinct and divergent angular direction, with respect to a direction substantially parallel to the central longitudinal axis of the cannula.

9. The multi-spot, multi-fiber, laser probe of claim 8, wherein the distal pass-through element comprises an additional channel extending through the distal pass-through element at or near the central longitudinal axis of the cannula, and wherein the laser probe further comprises an additional optical fiber extending from the proximal end of the laser probe to at least near the distal end of the laser probe, through the additional channel, so that the additional optical fiber is positioned to emit light in the direction substantially parallel to the central longitudinal axis of the cannula.

10. The multi-spot, multi-fiber, laser probe of claim 8, wherein the distal end of each of one or more of the plurality of optical fibers is flat cleaved.

11. The multi-spot, multi-fiber, laser probe of claim 8, wherein the distal end of each of one or more of the plurality of optical fibers is flat polished, to an end-angle of less than about 5 degrees.

12. The multi-spot, multi-fiber, laser probe of claim 8, wherein each of one or more of the plurality of fibers has a tapered cross-sectional profile along a portion of the respective fiber at or near the distal end of the respective fiber.

13. The multi-spot, multi-fiber, laser probe of claim 12, wherein the tapered cross-sectional profile for at least one of the one or more of the plurality of fibers tapers to a larger cross section near the distal end of the respective fiber, relative to a cross section further from the distal end of the respective fiber.

14. The multi-spot, multi-fiber, laser probe of claim 12, wherein the tapered cross-sectional profile for at least one of the one or more of the plurality of fibers tapers to a smaller cross section near the distal end of the respective fiber, relative to a cross section further from the distal end of the respective fiber.

* * * * *